(12) United States Patent
Schneider et al.

(10) Patent No.: US 12,264,309 B2
(45) Date of Patent: Apr. 1, 2025

(54) METHOD OF PRODUCING MYCELIUM TEXTILE FABRIC AND FABRICS AND PRODUCTS MADE THEREBY

(71) Applicant: ISA TanTec Limited, Macau (CN)

(72) Inventors: Thomas Schneider, Heshan (CN); Reiner Hengstmann, Erlangen (DE)

(73) Assignee: ISA TanTec Limited, Macau (CN)

( * ) Notice: Subject to any disclaimer, the term of this patent is extended or adjusted under 35 U.S.C. 154(b) by 756 days.

(21) Appl. No.: 17/357,537

(22) Filed: Jun. 24, 2021

(65) Prior Publication Data

US 2021/0403857 A1  Dec. 30, 2021

Related U.S. Application Data

(60) Provisional application No. 63/044,004, filed on Jun. 25, 2020.

(51) Int. Cl.

| | |
|---|---|
| C12N 1/14 | (2006.01) |
| C12M 1/00 | (2006.01) |
| C12M 1/12 | (2006.01) |
| C12M 1/34 | (2006.01) |
| D06M 16/00 | (2006.01) |
| D01F 13/00 | (2006.01) |
| D06M 101/02 | (2006.01) |

(52) U.S. Cl.
CPC ............ *C12N 1/14* (2013.01); *C12M 23/04* (2013.01); *C12M 23/38* (2013.01); *C12M 25/00* (2013.01); *C12M 41/12* (2013.01); *D06M 16/00* (2013.01); *D01F 13/00* (2013.01); *D06M 2101/02* (2013.01)

(58) Field of Classification Search
None
See application file for complete search history.

(56) References Cited

U.S. PATENT DOCUMENTS

2018/0014468 A1* 1/2018 Ross ................... C05F 9/04
2020/0120880 A1  4/2020 Ross et al.

FOREIGN PATENT DOCUMENTS

| CN | 101627127 A | 1/2010 |
|---|---|---|
| WO | WO2020115690 A1 | 6/2020 |

OTHER PUBLICATIONS

Written Opinion of the International Searching Authority corresponding to PCT/CN2021/102495 dated Sep. 27, 2021.
International Search Report dated Sep. 27, 2021 corresponding to Application No. PCT/CN2021/102495.
"The Fungi in Your Future", YouTube, SciFri, Nov. 16, 2016, https://www.youtube.com/watch?v=jBXGFOk5_Rs.

(Continued)

*Primary Examiner* — David W Berke-Schlessel
(74) *Attorney, Agent, or Firm* — HOGAN LOVELLS US LLP

(57) ABSTRACT

A system and method for creating mycelium textile materials is disclosed, in which leftover, cutoff, and other materials used to create the textile materials that would otherwise be discarded are further used in a second process to create bonded mycelium boards. The system and method further reuse or recycle materials throughout the process of creating the mycelium textile fabric and bonded mycelium boards, thus keeping waste to a minimum.

7 Claims, 5 Drawing Sheets

(56) References Cited

OTHER PUBLICATIONS

Brooke Roberts-Islam, "Mushroom-Based 'Leather' Is Now A Scalable Alternative To Animal Leathers, Poised For Market Disruption", Apr. 1, 2021, Forbes, https://www.forbes.com/sites/brookerobertsislam/2021/04/01/mushroom-leather-is-now-a--scalable-alternative-to-animal-leathers-poised-for-market-disruption/?sh=a36b5e25b195.

"Mushrooms Are Now The New Leather!", YouTube, CNA Insider, Mar. 18, 2020, https://www.youtube.com/watch?v=ykWIACD6u8E.

"How Mushrooms Are Turned Into Bacon And Styrofoam", YouTube, Business Insider, Apr. 11, 2021, https://www.youtube.com/watch?v=uznXI8wrdag.

Jones et al. "Engineered mycelium composite construction materials from fungal biorefineries: A critical review", ScienceDirect, vol. 187, Feb. 2020.

"Commercial Stainless Steel Rectangular Large Hi-Side Lock Clips Lasagna Baking Bakeware Roasting Cooking Sheet Tray Roaster Pan for Oven with Lid and Handle," Screen Shot, available at https://www.amazon.com/PROFESSIONAL-Commercial-Stainless-Rectangular-Bakeware/dp/B07FK4G7PD.

Deeg et al., "Greener Solutions: Improving performance of mycelium-based leather", PH 290—Greener Solutions Fall 2017.

\* cited by examiner

601
Sample
Mycelium Board

METHOD OF PRODUCING MYCELIUM TEXTILE FABRIC AND FABRICS AND PRODUCTS MADE THEREBY

RELATED APPLICATION

This application claims priority to U.S. provisional application 63/044,004 filed on Jun. 25, 2020, the contents of which are incorporated by reference in their entirety.

FIELD OF THE INVENTION

The present invention relates to a system and method of producing mycelium textile fabrics, mycelium textile fabrics, and products made from the mycelium textile fabrics. In particular, the invention relates to a method of producing a mycelium material in a bioreactor, followed by vacuum treatment of the soaked mycelium material, wherein condensate from the vacuum process is collected and re-used for further treatments of additional mycelium material in a closed loop process.

BACKGROUND OF THE INVENTION

Mycelium is the vegetative part of a fungus, comprising a network of branching, threadlike hyphae. Mycelium is also called the root of a mushroom. Due to its insulating and moisture absorbing properties, mycelium has been used in creating textile fabrics. These textiles have been formed from mycelium alone, or mycelium as grown or combined with other woven and non-woven materials. However, current processes to grow and create mycelium fabrics often result in waste materials or cutoffs, generated during multiple steps to go from growing the mycelium in a reactor to having a final fabric product, that go unused.

What is needed is a process to create mycelium fabrics that increases the efficiency and effectiveness of forming mycelium fabric panels, and that eliminates or reduces the waste of raw materials and unused cuttings of the mycelium fabric in the overall process from creation of mycelium fabric to finalization of consumer products made from such fabric.

SUMMARY OF THE INVENTION

The present invention is directed to a system and method for creating mycelium textile materials, the mycelium textile materials resulting from the method, and products made from the mycelium materials. In addition, following the process used to create the mycelium textile materials and products formed thereof, processing leftover and cutoff materials used in a second process to create bonded mycelium boards. The system and method re-use or recycle materials throughout the process of creating the mycelium textile fabric and bonded mycelium boards, thus keeping waste to a minimum.

The system and method described herein are directed to production of natural mycelium textile fabric, with re-use of left over material and cutoffs that would otherwise be discarded being used to produce bonded fiber boards. The resulting mycelium textile fabric may be used to produce footwear, apparel, and accessories. As described herein, system and method for creating the mycelium textile fabric and products made therefrom begins with growing of mycelium in a bioreactor. A substrate is provided in the bioreactor for growing the mycelium, and a non-woven or woven fabric material may also be included in the bioreactor to act as a growing support backing for the mycelium. The mycelium is fed with a solution in order to avoid digestion of the fabric while in the bioreactor. Once a desired amount of mycelium has grown in the bioreactor, the mycelium, and any backing material used in the bioreactor, are harvested from the bioreactor and processed.

As part of the processing, the mycelium material with or without the backing are pasteurized and dried. Depending on the thickness, the mycelium material may be cut into a required thickness. The resulting mycelium material from the processing may be used as-is, or may continue to be processed into panels and assembled into final products. For example, where treatment solutions or agents, such solutions to provide a desired color or texture, are added in the bioreactor to treat the mycelium material, the material may then be subjected to vacuum and temperature applications in order to improve the penetration of the treatment solutions into the mycelium body. As noted here, the bioreactor process may be implemented as a closed-loop system, such that any treatment solution that is removed during the vacuum and temperature process is re-fed back into the bioreactor for use as a treatment solution for the next batch of mycelium material being grown and treated in the bioreactor. When the vacuuming and temperature applications are complete, treated panels of mycelium material (with or without the fabric backing) are removed and then pressed. These panels may be coated with a biopolymer if required. These fabric sheets are then cut and, if desired, prepared into final consumer products.

During the processing of the mycelium material in the bioreactor, there may be processing leftovers after the initial processing and slicing of the mycelium material (and any backing material) before applying the vacuum and temperature applications. In addition, after the final mycelium panels are cut, there are mycelium cutting leftovers. To ensure there is minimal to no waste from the procedure of creating the mycelium fabrics, these processing leftovers and cutting leftovers may be used in a second process where the leftovers are formed into bonded mycelium boards. In particular, the leftovers may be shredded or ground to achieve a desired particle size, combined with filler materials such as cork, saw dust, natural fibers, or rice husk, and mixed to create a viscose mixture. The viscose mixture may be applied to a backing material, which is then pressed, dried and cut into bonded mycelium board products.

DETAILED DESCRIPTION OF THE INVENTION

The system and method described herein are directed to production of natural mycelium textile fabric, with re-use of left over material and cutoffs that would otherwise be discarded being used to produce bonded mycelium boards. The resulting mycelium textile fabric may be used to produce footwear, apparel, and accessories. As described herein, the mycelium fabric may be created with or without a plant based or semi-synthetic non-woven fabric backing. When a non-woven fabric backing is used, the non-woven fabric acts as a growing support for the mycelium, or is laminated onto the mycelium. The mycelium material is grown in a bioreactor, with desired treatment substances applied while the material is in the bioreactor. The material may then be removed, and put into a heated vacuum system to improve the penetration of the treatment solutions, producing mycelium panels. These panels are then pressed, coated with a biopolymer (if required), and cut and prepared into final products. In order to reduce or eliminate waste during this process, treatment solutions and other additives removed during the vacuum process are gathered, and fed back into the bioreactor to treat the next batch of mycelium material. Moreover, any leftover materials from the processing or cutting of the mycelium material are used in a process to create bonded mycelium boards.

Figure 1A:
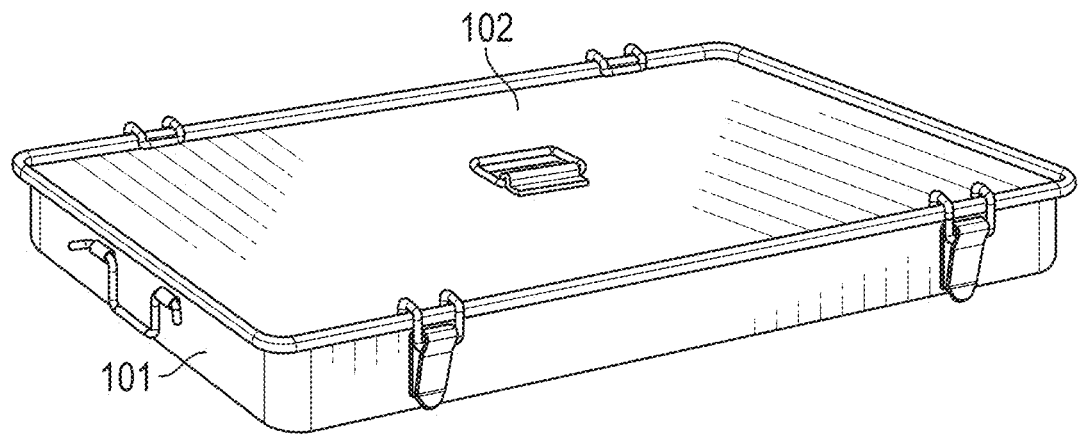
FIGS. 1A and 1B illustrate a bioreactor used to grow mycelium material.
Figure 1B:
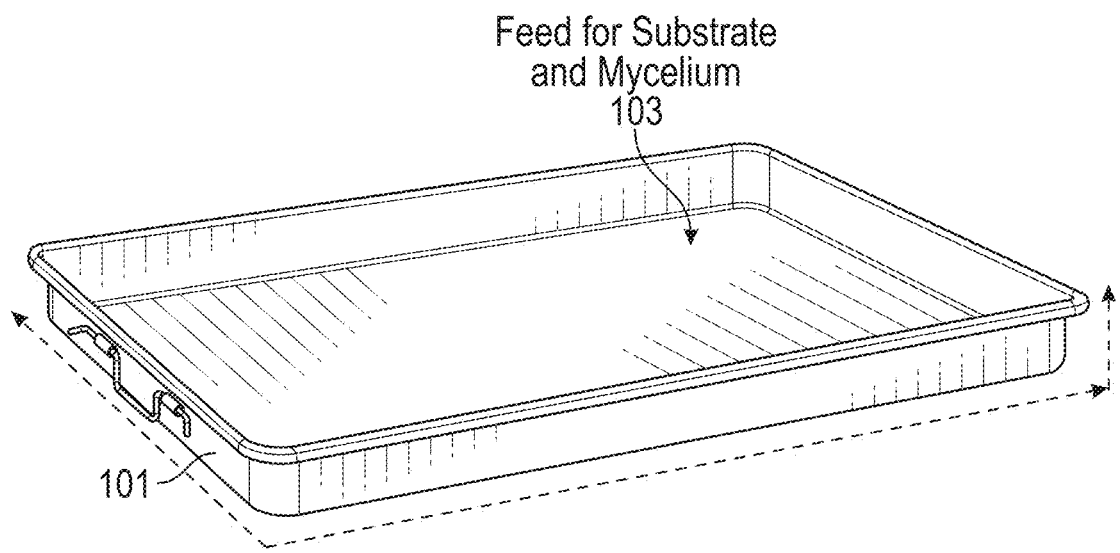

As shown in FIGS. 1A and 1B, the mycelium is grown or inoculated in a bioreactor. As shown in FIG. 1A, the bioreactor may include a tray 101 and a lid 102. The bioreactor may be made from stainless steel, or could be made from a polymer material such as plastic or rubber. The bioreactor may include a lid, although the growth or inoculation of the mycelium could also be completed in a bioreactor having no lid, as shown in FIG. 1B. The mycelium grows best when in a dark environment, and thus the bioreactors themselves may be placed in a dark area for growth. As noted, the bioreactor may also include a lid 102 in order to create a dark area inside the bioreactor tray 101 in which the mycelium grows. While a single tray is shown in FIGS. 1A and 1B, the bioreactors may also include several trays attached to or supported on the interior walls of the bioreactor, and the mycelium may be cultivated on the trays. Alternatively, multiple bioreactors can be separately used to grow mycelium, with the separate bioreactors being stacked on a shelf system while the mycelium is grown. A substrate or feedstock 103 on which the mycelium will grow is included within the bioreactor. This substrate or feedstock 103 may be, for example, sawdust, rubber hard wood, risk husk, or other organic materials. When the bioreactor is used, all necessary hygienic, sterile and temperature-controlled measures for the growing of the mycelium will be kept in place and strictly followed. After the desired amount of mycelium has grown, the pure mycelium or mycelium composite, in the form of a panel, may be removed from the one or more trays of the bioreactor.

Figure 2:
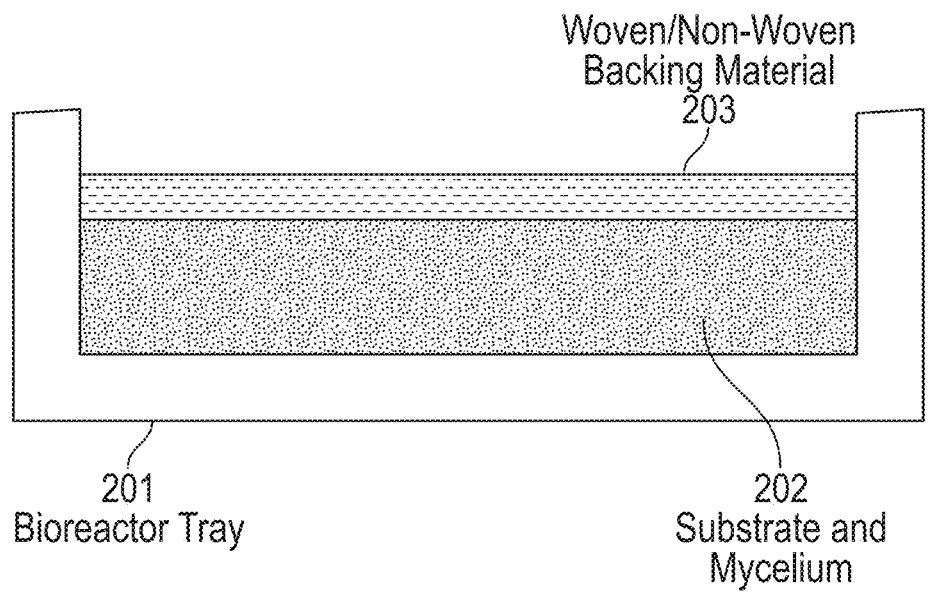
FIG. 2 illustrates growing mycelium material in a bioreactor, with the use of woven or non-woven fabric as a backing.

As shown in FIG. 2, a fabric material 203 may be included in the bioreactor 201 to use as a support and backing for the growth of the mycelium. As shown in FIG. 2, the mycelium and substrate material 202 may be included in the bioreactor tray 201, with the fabric backing material 203 placed on top. Alternatively, the fabric backing material 203 may be placed on the bottom of the bioreactor tray 201, with the substrate and mycelium 202 then included on top of the backing material 203. When grown with a backing material 203, the result is not pure mycelium, but is instead a mycelium composite material. This fabric backing material 203 may be a woven or non-woven fabric. For example, a non-woven fabric made out of natural fibers such as, for example, hemp, jute, pineapple leaves fibers, linen, ramie, water hyacinth fibers, coconut fibers may be used. Alternatively, a semi-synthetic fiber such as viscose of lyocell, preferably made out of pre- and post-consumer cotton waste or at least containing up to 50% pre- and post-consumer cotton waste may be used for the backing. As another example, a blend of non-woven materials may be added to the feedstock or to the surface of any substrate in the bio reactor, with such feedstock or substrate together with the non-woven materials forming the backing for the mycelium to grow on. Once the mycelium has grown to a desired size, the growth is stopped and treatment such as pasteurization and drying applied to create mycelium or mycelium composite panels.

After the mycelium or mycelium composite panel is initially grown in the bioreactor as described with respect to FIGS. 1A, 1B and 2, the mycelium or mycelium composite panels are transferred to a treatment reactor where treatment substances may be added to treat the mycelium or mycelium composite panels. This treatment reactor may be a tray, vat, or other container. If desired, dye may also be added in the treatment reactor. Alternatively, a separate dye tray may be provided. The mycelium or mycelium composite panels are giving sufficient time to soak and the chemical substances making up the treatment solutions time to react. For example, the panels may be left to soak in the treatment reactor for 60-90 minutes. Following this application of treatment and dying substances, the mycelium or mycelium composite fabric material may be transferred to a vacuum and heating system.

Figure 3:
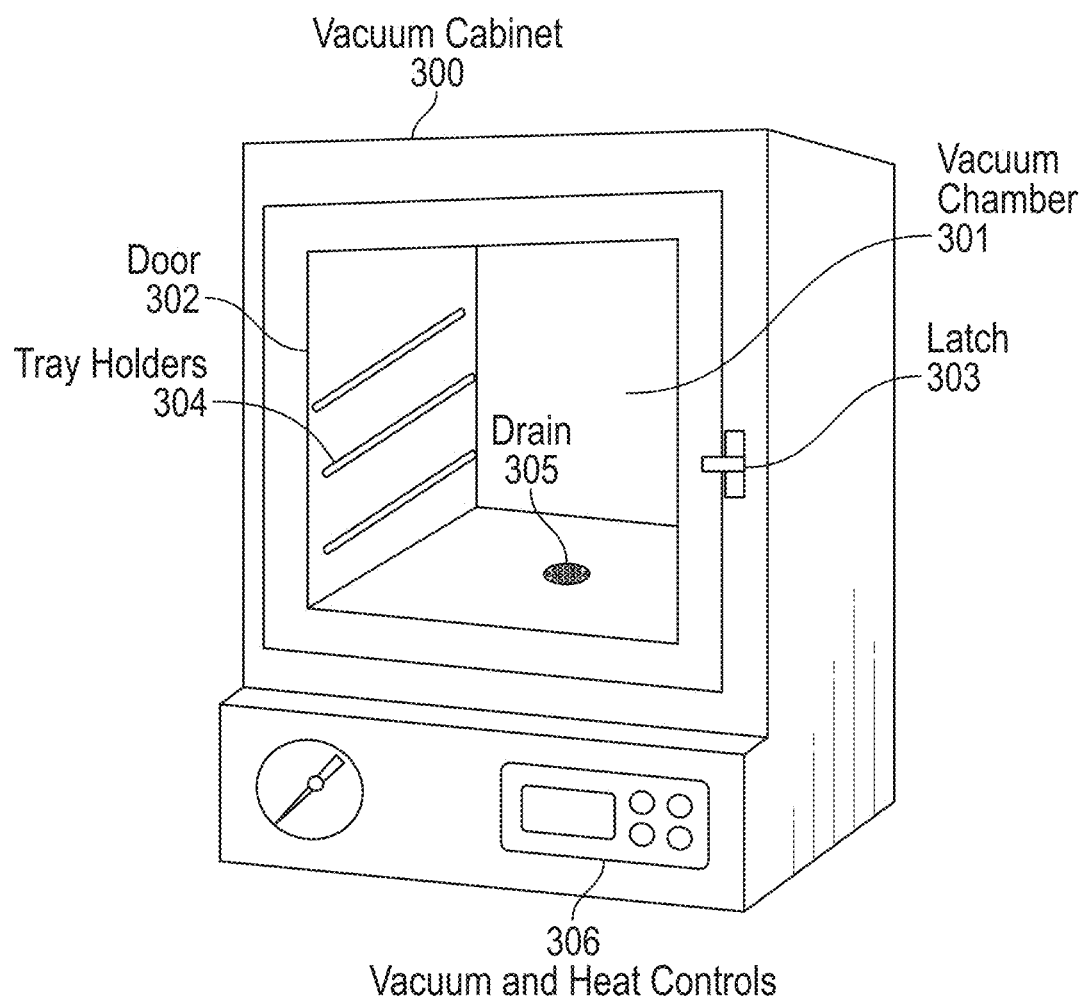
FIG. 3 illustrates applying vacuum treatment to a mycelium material.

The vacuum and heating system may be, for example, a tempered vacuum cabinet. As shown in FIG. 3, the vacuum and heating system may be a temperature controlled vacuum cabinet 300. The vacuum cabinet 300 may include a sealed chamber 301 in which the mycelium or mycelium composite material is placed. A door 302 may be provided on the vacuum cabinet, which provides access to the vacuum chamber 301. When closed, a latch 303 may be provided to keep the door 302 secure and the chamber 301 sealed during use. Tray holders may be provided on the walls of the vacuum chamber, allowing a user to insert multiple reactor trays into the vacuum cabinet at the same time. In use, the chamber 301 may be sealed, and a vacuum pump initiated to remove air from the chamber, thereby compressing the mycelium or mycelium composite material and improving the penetration of the treatment substances. This helps to ensure a more complete reaction of the treatment substances with the mycelium. The vacuum pump may be, for example, a membrane vacuum pump connected to the vacuum chamber. In addition, a controlled heating element may be included to heat the mycelium or mycelium composite material while in the chamber, further enhancing penetration of the treatment substances. Vacuum and heat controls 306 may be provided on the vacuum cabinet in order to allow users to adjust the vacuum pressure and temperature of the vacuum cabinet, including turning on and off the vacuum and heating elements. The panels may be pressed into a desired shape prior to applying the heating, such that the panels dry in the desire shape. Alternatively, the panels may be air dried, vacuum dried, or dried with a combination of heat, air drying, and vacuum drying. The vacuum and heating system may further include a drain 305 leading to a collection tray (not shown), in which any treatment substances, such as known biodegradable treatment agents in the textile and leather industries, and other processing agents removed from the mycelium or mycelium composite during the process are collected. The collection tray may be included in an interior space of the vacuum cabinet, or positioned below the vacuum cabinet.

Following the vacuum and temperature treatment, the mycelium or mycelium composite material may be formed into panels, if not already in panels after removal from the vacuum and heating system. These panels are then pressed and further processed to create final fabrics or consumer goods.

Figure 4:
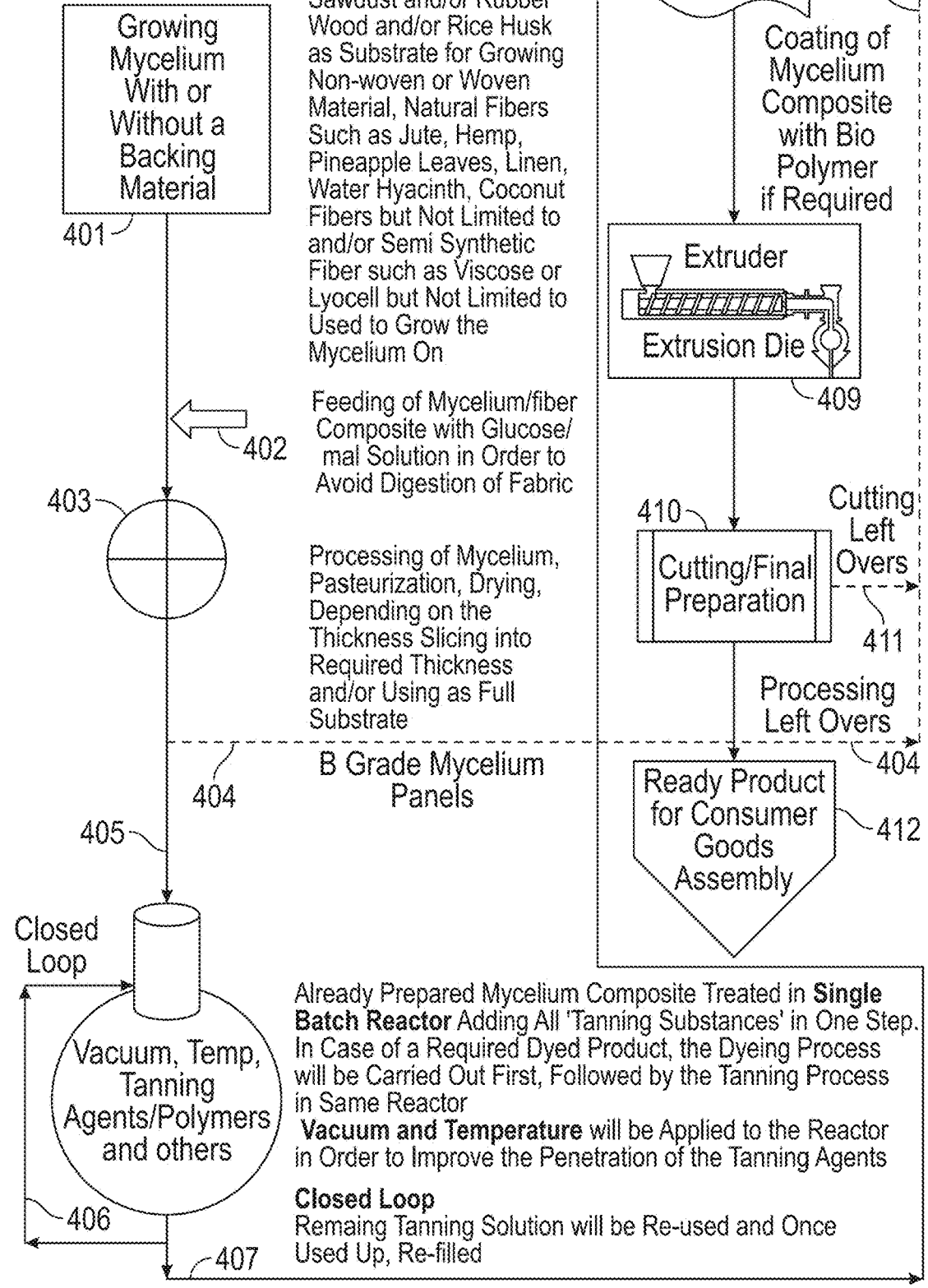
FIG. 4 provides a flow diagram of the process of creating mycelium textile materials and products.

FIG. 4 illustrates a flow diagram of the process used to grow mycelium and create pure mycelium or mycelium composite panels that are ultimately cut into fabric panels or processed into consumer goods. As shown in FIG. 4, mycelium is first grown or inoculated in a bioreactor at 401, such as the bioreactor shown in FIGS. 1A, 1B and 2. As mentioned, the bioreactor may be made from stainless steel or a polymer. One or more trays may be included within the bioreactor, on which the mycelium is grown. The bioreactor may contain a lid, as shown in FIG. 1A, which may be open or closed during the growth of the mycelium. In addition, the bioreactor may be open with no lid. As discussed above, FIG. 1A illustrates a bioreactor with a lid on to ensure a dark environment for mycelium growth, and FIG. 1B illustrates a bioreactor with no lid on. A substrate or feedstock for the mycelium is added to the one or more trays in the bioreactor. This substrate or feedstock may be, for example, sawdust, rubber hard wood, risk husk, or other organic materials. Before and during the growth of the mycelium, all necessary hygienic, sterile and temperature-controlled measures for the growing of the mycelium will be kept in place and strictly followed.

During the growth of the mycelium as shown at 401, a non-woven or woven fabric material as described with respect to FIG. 2 may be include in the bioreactor to included, such that the mycelium has a surface on which to grow. When a non-woven or woven backing material or substrate is used, the mycelium grows into the fabric and anchors the mycelium during the growth process. That is, the mycelium "roots" into the backing or substrate material while creating a stable mycelium composite. Partial digestion of the non-woven fabric material may be avoidable, and is considered part of the mycelium growth process.

At 402, the mycelium or mycelium composite is fed with a glucose or malt solution in order to avoid a complete digestion of the cellulose on which the mycelium grows. In particular, where a non-woven or backing material is used, a solution containing glucose and/or malt may be used as a spray to frequently create an additional substrate mist. This substrate mist is an additional food source for the mycelium during the growth process, and further helps to avoid the complete digestion of the non-woven backing or substrate material by the mycelium during growth. While the glucose or malt solution is being applied, strict temperature, humidity, and sterile conditions are maintained.

The growing process is continued to cultivate mycelium and/or mycelium-fungi in the bioreactor until it reaches a desired size. For example, a mycelium and/or mycelium-fungi intermediate may be cultivated in bioreactor until it reaches a size of up to 2 m². The mycelium intermediate is a stage of growth that not yet a final fungi, but is more growth than the mycelium root structures of the fungi.

Once the desired size is reached, further processing is applied at 403 to stop the growing process and pasteurize the mycelium or mycelium composite material. As part of this processing 403, the mycelium or mycelium composite may be pasteurized and dried into panels. Depending on the desired size of the panels, they may be further sliced or cut into panels of a desired thickness or shape. For example, once the desired thickness and quality of the pure mycelium, or mycelium composite, and/or mycelium intermediate is achieved, the growing process is stopped. For example, a desired panel at this stage in the process may have a thickness of 2-9 cm. Such thickness may be achieved after, for example, 5-9 days, after which the growing process is stopped. The mycelium panels with or without non-woven (or woven) fabric backing support will be harvested in a fully automated, semi-automated of manual system for further processing. To harvest the panel, the grown panel is carefully cut off from any substrate in and then further processed. If there is a backing material, the mycelium is removed from both the backing material and the substrate. Any remaining substrate can be reused as the substrate feedstock on additional cycles of growing mycelium, until it is used up and new feedstock added. In addition, the remaining substrate can be mixed with new feedstock materials in later cycles of growing mycelium. The still living mycelium organism, now as a mycelium composite panel with the non-woven fabric supported panel, or as a panel of pure mycelium, will be pasteurized using controlled temperatures in order to stop the growing process. The remaining water in the mycelium panels is then removed using drying ovens, forced air driers, or other drying elements and techniques.

The results after the processing shown at 403 are mycelium panels. These mycelium panels may be graded based on desired quality or characteristics. Panels judged to be of a sufficient grade may be sent for further processing as shown at 405. Panels judged to be of a lesser grade may be separated at 404, and included as part of leftover materials 413 used in other processes. For example, a panel that does not have the appropriate thickness or uniformity may be judged to be of lesser grade, such as being given a designation as a B grade panel, and separated at 404 for use as part of leftover materials 413.

For example, higher graded panels sent for further processing at 405 may be dried and either used as a whole panel, or depending on the thickness, the upper surface and/or lower surface may be cut off. For example, a vertical band saw may be used to perform any necessary cutting. Any cutoffs from this step will be recycled, and become part of leftover materials 413 that can be used in other processes so that they do not go to waste. The prepared higher grade panels, with or without the surfaces, may be further treated in such a way to achieve a "leather" like mycelium based textile material. This may be achieved with the use of natural based treatment substances, including those that react in with the N-acetoamide functional group of the chitin which serves as the inner structure, or skeleton, of the mycelium through a reaction such as deacetylation of the chitin molecule. The reaction could also be, for example, with the chitosan molecule, where its —$NH_2$ functional group will be the reaction point for further possible polymerization reactions amongst the chitosan molecules. Another possibility is to add of natural latex, preferably derived from dandelion, that does not cause allergic reactions. Another possibility may be the in-situ polymerization within the mycelium structure while creating Polyhydroxy Alkanoates, PHA, where the —OH groups of the chitin molecule will be the functional groups for the polymerization.

When additional processing 405 is desired, the panels may be treated with various treatment substances to achieve desired color and texture. The already prepared mycelium or mycelium composite panels may be treated in a single batch bioreactor, where the treatment substances are added all in either once or in stages. The decision of whether the treatment substances are added all at once or in stages may depend on the expected reaction of the mycelium and the treatment solution. Once all treatment substances are added to the reactor system, the mycelium or mycelium composite panel will be soaked in the solution. While the panel is soaking, the treatment substances may be gently mixed. The panels may be soaked for a desired amount of time until the treatment substances penetrate the mycelium or mycelium composite panels. For example, the panels may be soaked in the treatment substances, such as tanning solution, for 3-4 hours or shorter while gently mixing the system. In addition, dyes may be added to the bioreactor to dye the mycelium or mycelium composite panel to a desired color. When both dyeing and tanning are implemented, the dyeing may be carried out first, followed by the tanning process within the same single batch bioreactor.

Also as part of 405, the panels may then be added to a heated vacuum system. In the heated vacuum system, a vacuum and heating process may be applied to the panels in order to improve the penetration of the treatment substances, such as fat liquors, into the panels. For example, in order to achieve a more complete penetration of any liquid treatment agents used, the soaked mycelium composite or pure mycelium panels together with remaining treatment liquid as described above may be transferred into a heated vacuum system where a vacuum will be applied. This vacuum may be applied for a predetermined or customizable time period, while also heating the panels with heating element. For example, the vacuum may be applied for 30-40 minutes with operating at a treatment temperature of 40-50° C. in order to reduce the viscosity of the treatment solution.

As shown at 406, there may be remaining treatment substance liquid or condensate remaining after the vacuum and heating process. This remaining liquid and condensate are collected, such that they can be reused with the next batch of panels subjected to the vacuum and heating process. In this manner, the system operates as a closed loop system where remaining liquid or possible occurring condensate from the vacuum process is collected and reused for further treatments. This helps to reduce waste and materials used in the process. For example, fresh treatment solutions are added only if needed, due to the initial treatment solutions added within the closed-loop process being used up. This helps to reduce wastewater and pollution from the entire process of forming the mycelium or mycelium composite fabrics.

After the vacuum and heating process is complete, the resulting panels are removed from the heated vacuum system at 407 and prepared for further processing. At 408, the panels undergo a pressing process, where the remaining liquid, including any remaining treatment solution or dyes, will be pressed out and collected. For example, the panels may be applied onto a fabric, spread and allowed to at least partially dry. These may then be pressed using, for example, a hydraulic press or rollers. The collected treatment solution may again be re-used for treating additional panels as part of the closed-loop process. After pressing, the panels are dried and prepared for further processing. At 409, the panels may optionally be coated with a coating, depending on the desired future application of the mycelium or mycelium composite fabric panels. For example, the surface of the mycelium or mycelium composite fabric panels may be coated with a bio-based and bio-degradable coating, such as a coating made of the bio polymer casein, such as bio degradable Polyurethanes and/or Polyester. The applied coatings may provide additional strengthening characteristics to the fabric panels, or can create or enhance characteristics on the surface of the fabric panels, such as making the panels appear to have a shiny or matte finish, or to apply a color coating to the surface of the panels. The coatings may also make the fabric panels less abrasive. This coating may be applied as part of extrusion process, where an extruder forces the coating material through an extrusion die onto the fabric. The fabric may be moved under the extruder such that the entire fabric is coated and infused with the coating. Coatings may also be spray applied, applied with brushes, or applied by dipping or soaking the fabric panels in a coating substance.

After any desired coating is applied, the mycelium or mycelium composite panels are then cut or otherwise prepared for final uses, as shown at 410. For example, the fabric panels may be cut to desired shapes and sizes for further use. The final treated mycelium or mycelium composite panels may be cut onside, or otherwise prepared for further use as apparel or accessories. As part of this processing, any portions of the fabric panels that are cut or removed are gathered as cutting leftovers at 411. These cutting leftovers may be combined with the leftovers from the initial processing the mycelium or mycelium composite when formed into Grade B panels at 404. The leftovers of the Grade B panels at 404 and the cutting leftovers at 411 may be combined to create process leftovers at 413. These process leftovers may be used to create additional products so they are not wasted, as described herein.

At 412, the mycelium or mycelium composite panels are finalized as a product for use as a fabric or for assembly into consumer products. For example, the consumer products may include apparel, accessories, or footwear.

Figure 5:
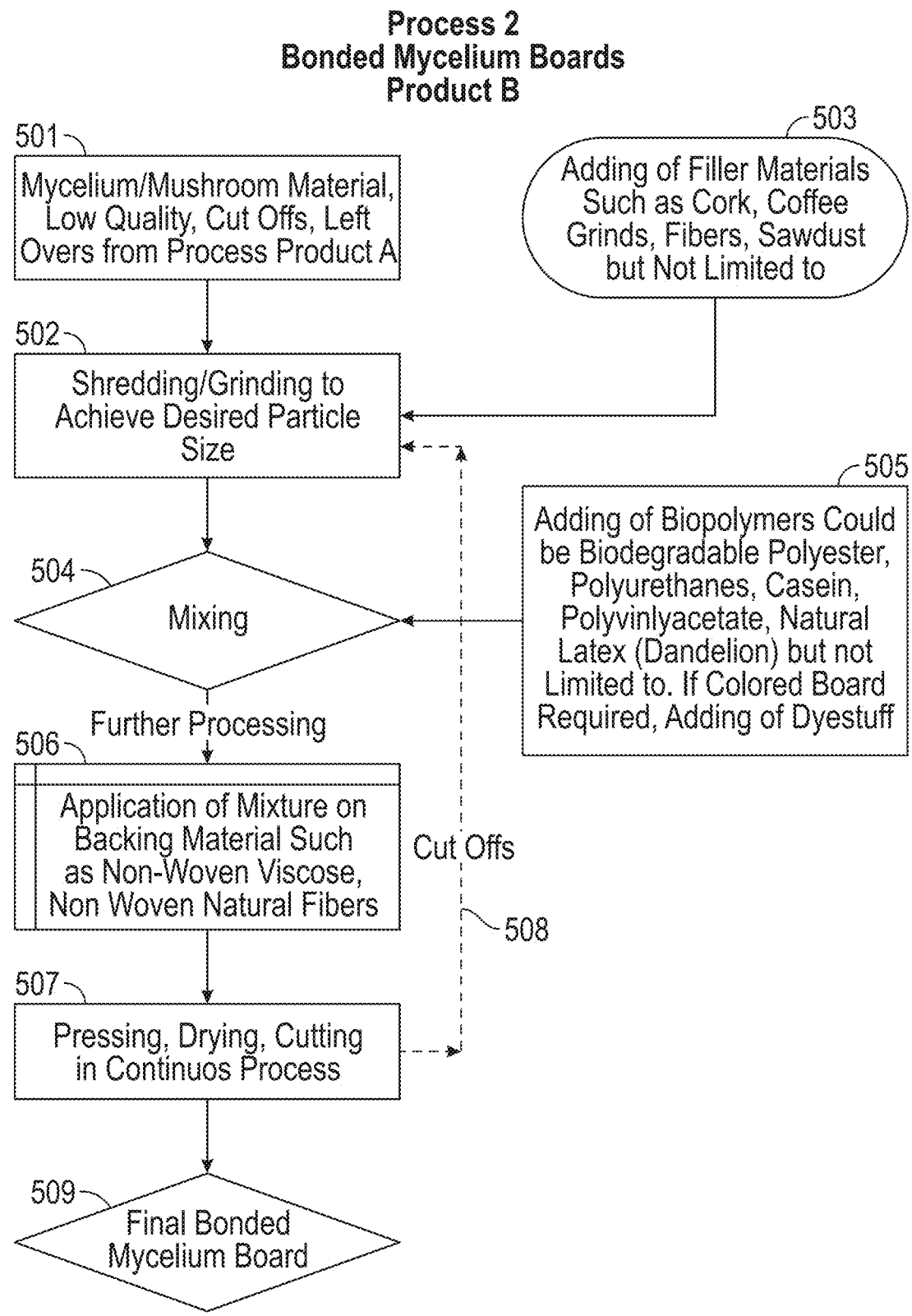
FIG. 5 provides a flow diagram of the process for processing left over and cutoff materials from the process shown in FIG. 4 to produce bonded mycelium boards.

As noted above, the results of this process of forming final mycelium or mycelium composite fabrics include certain leftovers 413. Rather than letting these leftovers go to waste, they may instead be used in additional processing to create further products. For example, any material left over due to the slicing processes and or cutting processes in forming the mycelium or mycelium composite materials may be re-used in a recycling process. As shown in FIG. 5, for example, these leftovers may be used in a process to create bonded mycelium boards. At 501, the leftover materials from the creation of the mycelium or mycelium fabric are gathered and prepared as starting material 501 for conversion to bonded mycelium boards. These materials may include, for example, cut off or sliced mycelium material (with or without a backing material), low quality material, cutoffs, or other leftovers from the process described with respect to FIG. 4. The starting material for the process at 501 may also include B grade mushrooms or other materials. B grade mushrooms are mushrooms that, for example, are no longer feasible for food purposes, do not meet a desired quality standard to be sold to consumers, or are left overs from shops and stores that, due to shelf life, can no longer be sold. B grade mushrooms may also include any mushrooms that would otherwise be disposed of. At 502, these starting materials are shredded or ground down to a smaller size, such as a fiber length of a few millimeters. Any shredded raw material fibers will be treated with remaining treatment solution from processes described with respect to FIG. 4 or other additives, if desired, and stirred to mix the raw materials with the treatment solution. For example, the different left over treatment solutions mixed with different dyes may be of different colors. These can be saved, and when a particular color bonded mycelium board is desired, the leftover treatment solution and dye of that particular color can be retrieved and mixed in with the shredded fiber material at this step. After the treatment is complete, the treated mixture will remain in a mixing bath for finalizing of the reaction. These treated fibers are called Number 1 fibers. Material cut offs from already treated mycelium composites or pure mycelium products will be shredded or ground in the same way as describes above, but these will not treated with the treatment solution. These fibers are called Number 2 fibers. Any remaining backing material included in the leftovers may act as reinforcement when these leftovers are formed in a final product. At 503, filler materials are added with the shredded or ground fibers, including the Number 1, Number 2 fibers, or both. These filler materials may include, for example, cork, coffee grinds, natural fibers, or sawdust. The combined shredded or ground fibers and filler material is then mixed at 504. During the mixing, additives may be included and mixed with the shredded or ground fibers and filler material as shown at 505. The additives may include, for example, biopolymers, bio-based polymers which are biodegradable, biodegradable polyester, polyurethanes, casein, polyvinlyacetate, and/or natural latex (dandelion). As mentioned above, additional cellulose fibers remaining from any mycelium non-woven fabric composite will act here as fill material and as possible reinforcement of the final product. If a colored board is desired as the final product of the process shown in FIG. 5, then dyes may also be added during this mixing step.

At 506, the fiber and biopolymer or other additive mixture is then applied on a backing material. This backing material may include, for example, a non-woven or woven materials. The non-woven materials may include non-woven viscose or non-woven natural fibers. The fiber/additive mixture will be applied to the backing material in a desired amount of thickness in order to achieve a desired strength of the resulting bonded mycelium board.

At 507, combination of the mixed fiber and additive material and backing material is pressed, dried, and cut. This may be performed as a continuous process, whereby the materials are first pressed to compress them together and put them into a proper shape for cutting, then dried, and finally cut to a desired size. For example, the materials may be pressed using a hydraulic press or rollers. Drying the materials may be achieved using, for example, an oven, vacuum drying, or air drying. As shown in FIG. 5, any cuttings made at this step may be collected at 508 and mixed back in with additional leftovers in the shredding and grinding step 502 in order to again minimize or eliminate waste. After the final combination of materials has been dried and cut, the resulting product is a bonded mycelium board as shown at 509.

Figure 6:
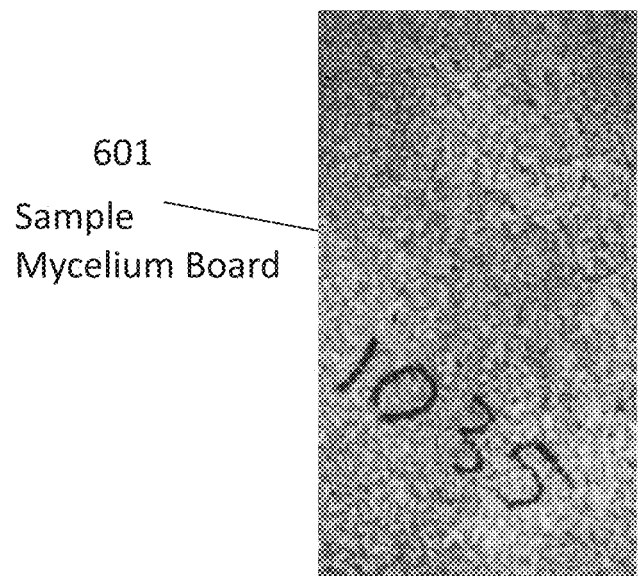
FIG. 6 illustrates a bonded fiber board produced from left over or cutoffs from the treated mycelium material.

FIG. 6 provides an illustration of a bonded mycelium board that may result from the process shown in FIG. 5.

The invention claimed is:

1. A system for creating mycelium fabric products, comprising:
   a bioreactor configured to grow mycelium;
   substrate or feeder materials provided in the bioreactor;
   a single batch reactor configured to receive grown mycelium panels;
   treatment solutions provided in the single batch reactor to treat the mycelium panels and create treated mycelium panels;
   a temperature controlled vacuum oven configured to receive treated mycelium panels, the temperature controlled vacuum oven including a drain leading to a collection tray, the collection tray configured to collect treatment solution removed from the treated mycelium panels while the treated mycelium panels are in the temperature controlled vacuum oven; and
   a cutting assembly.

2. The system of claim 1, wherein the bioreactor includes a lid.

3. The system of claim 1, further comprising a backing material provided in the bioreactor.

4. A method for producing mycelium products, comprising:
   providing a bioreactor tray;
   providing substrate or feed materials in the bioreactor tray;
   growing one or more mycelium panels in the bioreactor tray;
   stopping growth of the one or more mycelium panels;
   drying and slicing the one or more mycelium panels into a desired thickness;
   transferring the one or more mycelium panels to a single batch bioreactor;
   adding treatment solutions to the single batch reactor;
   removing the one or more mycelium panels from the single batch reactor;
   placing the one or more mycelium panels into one or more vacuum controlled ovens, the one or more vacuum controlled ovens including a drain leading to a collection tray configured to collect treatment solutions;
   applying vacuum and temperature control using the oven;
   collecting treatment solutions removed from the mycelium panels during the vacuum and temperature control in the collection tray of the one or more vacuum controlled ovens;
   pressing and cutting the mycelium panels; and
   reusing the collected treatment solutions to treat additional mycelium panels in the single batch reactor.

5. The method of claim 4, further comprising providing a backing material in the bioreactor during growth of the one or more mycelium panels.

6. A method for producing mycelium products, comprising:
   providing a bioreactor tray;
   providing substrate or feed materials in the bioreactor tray;
   growing one or more mycelium panels in the bioreactor tray;
   stopping growth of the one or more mycelium panels;
   drying and slicing the one or more mycelium panels into a desired thickness;
   transferring the one or more mycelium panels to a single batch bioreactor;
   adding treatment solutions to the single batch reactor;
   removing the one or more mycelium panels from the single batch reactor;
   placing the one or more mycelium panels into one or more vacuum controlled ovens;
   applying vacuum and temperature control using the oven;
   pressing and cutting the mycelium panels;
   collecting starting materials comprising one or more of cutoff mycelium panel material, unused mycelium panels, and leftover substrate and feed materials;
   reducing the starting materials to a desired particle size;
   mixing the reduced starting materials with biodegradable additives to create a mixture;
   applying the mixture to a backing material to create a combined mixture and backing material; and
   pressing, drying, and cutting the combined mixture and backing material to form bonded mycelium board.

7. The method of claim 6, further comprising:
   collecting cutoffs from the pressing, drying, and cutting of the combined mixture and backing material; and
   providing the collected cutoffs as starting materials.

* * * * *